United States Patent
Schneider et al.

(10) Patent No.: US 9,539,692 B2
(45) Date of Patent: Jan. 10, 2017

(54) MATERIAL REMOVAL FROM BALLOON CONE

(71) Applicant: Covidien LP, Mansfield, MA (US)

(72) Inventors: Mark Schneider, Mound, MN (US); Bradley Steele, Plymouth, MN (US)

(73) Assignee: Covidien LP, Mansfield, MA (US)

( * ) Notice: Subject to any disclaimer, the term of this patent is extended or adjusted under 35 U.S.C. 154(b) by 138 days.

(21) Appl. No.: 14/460,495

(22) Filed: Aug. 15, 2014

(65) Prior Publication Data

US 2016/0045275 A1 Feb. 18, 2016

(51) Int. Cl.
| | |
|---|---|
| *B24B 5/14* | (2006.01) |
| *A61M 29/00* | (2006.01) |
| *A61B 19/00* | (2006.01) |
| *B24B 19/00* | (2006.01) |
| *B24B 5/36* | (2006.01) |
| *A61M 25/00* | (2006.01) |
| *A61M 25/10* | (2013.01) |

(52) U.S. Cl.
CPC ............... *B24B 5/14* (2013.01); *A61B 19/34* (2013.01); *B24B 5/36* (2013.01); *B24B 19/009* (2013.01); *A61M 2025/0019* (2013.01); *A61M 2025/1031* (2013.01)

(58) Field of Classification Search
CPC ......... B24B 5/14; A61M 29/00; A61M 25/10; A61M 25/1002; A61M 2025/0019; A61B 19/34; A61B 19/00
USPC ................ 451/55, 180; 606/194; 604/103.08
See application file for complete search history.

(56) References Cited

U.S. PATENT DOCUMENTS

| | | | |
|---|---|---|---|
| 2,427,849 A | * | 9/1947 | Garwood .............. B24B 19/006 451/180 |
| 4,637,762 A | | 1/1987 | Acker |
| 4,738,055 A | * | 4/1988 | Jackson ............... B24B 19/226 451/180 |
| 4,906,244 A | | 3/1990 | Pinchuk et al. |
| 5,290,306 A | | 3/1994 | Trotta et al. |

(Continued)

FOREIGN PATENT DOCUMENTS

| | | |
|---|---|---|
| DE | 197 20 233 A1 | 11/1997 |
| WO | 0121381 A1 | 3/2001 |

(Continued)

OTHER PUBLICATIONS

International Search Report and Written Opinion for PCT/US2015/044427 dated Nov. 5, 2015, 14 pages.

*Primary Examiner* — Robert Rose

(57) ABSTRACT

A material-removing machine for removing material from a cone section of a medical balloon includes a material-removing element operatively connected to a prime mover such that operation of the prime mover imparts rotation to the material-removing element about a rotational axis. The material-removing element includes an interior surface defining a generally conical-shaped cavity extending along the rotational axis and adapted to receive at least a longitudinal portion of a cone section of an expanded medical balloon for removing material from the longitudinal portion of the cone section to reduce a wall thickness of the cone section. Material may be removed continuously around a 360-degree exterior perimeter of the longitudinal portion of the cone section of the medical balloon to reduce the thickness of the balloon wall defining the cone section.

20 Claims, 11 Drawing Sheets

(56) References Cited

U.S. PATENT DOCUMENTS

| | | | |
|---|---|---|---|
| 5,318,587 A | 6/1994 | Davey | |
| 5,334,146 A * | 8/1994 | Ozasa | A61M 25/1029 604/103.06 |
| 5,556,383 A | 9/1996 | Wang et al. | |
| 5,585,688 A | 12/1996 | DeKleine | |
| 5,733,301 A | 3/1998 | Forman | |
| 5,752,934 A | 5/1998 | Campbell et al. | |
| 5,769,817 A | 6/1998 | Burgmeier | |
| 5,797,877 A | 8/1998 | Hamilton et al. | |
| 5,797,878 A * | 8/1998 | Bleam | A61M 25/10 604/196 |
| 5,826,588 A * | 10/1998 | Forman | A61M 25/1029 128/898 |
| 5,830,182 A | 11/1998 | Wang et al. | |
| 5,833,657 A | 11/1998 | Reinhardt et al. | |
| 5,879,369 A | 3/1999 | Ishida | |
| 5,951,941 A | 9/1999 | Wang et al. | |
| 6,110,192 A | 8/2000 | Ravenscroft et al. | |
| 6,146,356 A | 11/2000 | Wang et al. | |
| 6,171,278 B1 | 1/2001 | Wang et al. | |
| 6,193,738 B1 * | 2/2001 | Tomaschko | A61M 25/10 606/194 |
| 6,200,290 B1 | 3/2001 | Burgmeier | |
| 6,287,506 B1 | 9/2001 | Hudgins et al. | |
| 6,358,227 B1 | 3/2002 | Ferrera et al. | |
| 6,406,457 B1 | 6/2002 | Wang et al. | |
| 6,488,654 B2 * | 12/2002 | Gonzalez | A61M 25/1027 216/8 |
| 6,620,127 B2 | 9/2003 | Lee et al. | |
| 6,866,649 B2 | 3/2005 | Ferrera et al. | |
| 6,896,842 B1 | 5/2005 | Hamilton et al. | |
| 6,951,675 B2 | 10/2005 | Chin et al. | |
| 7,048,712 B2 | 5/2006 | Chen et al. | |
| 7,074,206 B2 | 7/2006 | Lee et al. | |
| 7,306,616 B2 | 12/2007 | Eidenschink et al. | |
| 7,618,696 B2 | 11/2009 | Wang et al. | |
| 7,828,766 B2 | 11/2010 | Durcan | |
| 7,967,836 B2 * | 6/2011 | Warnack | A61M 25/1034 604/103.05 |
| 8,052,638 B2 | 11/2011 | Lee et al. | |
| 8,070,719 B2 | 12/2011 | Lee | |
| 8,268,418 B2 | 9/2012 | Gazza | |
| 8,292,913 B2 | 10/2012 | Warnack et al. | |
| 8,357,177 B2 | 1/2013 | Tomaschko et al. | |
| 8,394,055 B2 | 3/2013 | Durcan | |
| 2002/0018866 A1 | 2/2002 | Lee et al. | |
| 2003/0004535 A1 * | 1/2003 | Musbach | A61F 2/958 606/194 |
| 2007/0142772 A1 | 6/2007 | Deshmukh et al. | |
| 2010/0057001 A1 | 3/2010 | Chen et al. | |
| 2010/0178855 A1 | 7/2010 | Fukui et al. | |
| 2012/0016405 A1 | 1/2012 | Hamilton et al. | |
| 2012/0065718 A1 | 3/2012 | Simpson et al. | |

FOREIGN PATENT DOCUMENTS

| | | |
|---|---|---|
| WO | 03035158 A2 | 5/2003 |
| WO | 2006138741 A1 | 12/2006 |

* cited by examiner

MATERIAL REMOVAL FROM BALLOON CONE

FIELD OF THE DISCLOSURE

The present disclosure generally relates to a material-removing machine for removing material from a cone section of a medical balloon and a process for removing material from the cone section.

BACKGROUND OF THE DISCLOSURE

Balloons mounted on the distal ends of catheters are widely used in medical treatment. The balloon may be used to widen a vessel into which the catheter is inserted, open a blocked vessel and/or deliver a medical device to a body location among other uses. The medical balloon includes a central body section, which is typically tubular, opposite cone sections at opposite longitudinal ends of the body section, and opposite waist sections at opposite longitudinal ends of the balloon. In use, the uninflated balloon is delivered to a treatment location within a body lumen (e.g., a blood vessel) by tracking through an introducer sheath and exiting a distal end of the sheath to reach the treatment location. Once the uninflated balloon has reached the treatment location, fluid is delivered into the balloon, thereby expanding the outer circumference of the balloon (i.e., balloon is inflated). After treatment, the balloon is deflated and "pulled back" into the introducer sheath. The balloon catheter can then be withdrawn from the introducer sheath and the patient's body. It may be necessary or desired to re-introduce the balloon catheter into a body lumen, through the introducer sheath, to further treat the body lumen.

One known method of forming a medical balloon involves blow molding. In particular, the balloon is formed by radially expanding a segment of extruded polymer tubing, called a parison, in a mold. Balloons produced by radially expanding a parison typically have thicker waist sections and cone sections than the thickness of their body sections. The thicker cone sections may interfere with refolding of the balloon upon deflation (i.e., after treatment), which can make it difficult to pull the balloon back into the introducer sheath. This interference with re-folding may also make it difficult for the user to re-introduce the deflated balloon into the sheath after withdrawing the balloon catheter from the patient's body.

SUMMARY OF THE DISCLOSURE

In one aspect, a material-removing machine for removing material from a cone section of a medical balloon generally comprises a material-removing element operatively connected to a prime mover such that operation of the prime mover imparts rotation to the material-removing element about a rotational axis. The material-removing element includes an interior surface defining a generally conical-shaped cavity extending along the rotational axis and adapted to receive at least a longitudinal portion of a cone section of an expanded medical balloon for removing material from the longitudinal portion of the cone section to reduce a wall thickness of the cone section. Material may be continuously removed around a 360-degree exterior perimeter of the longitudinal portion of the cone section of the medical balloon to reduce the thickness of the balloon wall defining the cone section.

Other features will be in part apparent and in part pointed out hereinafter.

BRIEF DESCRIPTION OF THE DRAWINGS

Corresponding reference characters indicate corresponding parts throughout the drawings.

DETAILED DESCRIPTION OF THE DRAWINGS

Figure 1:
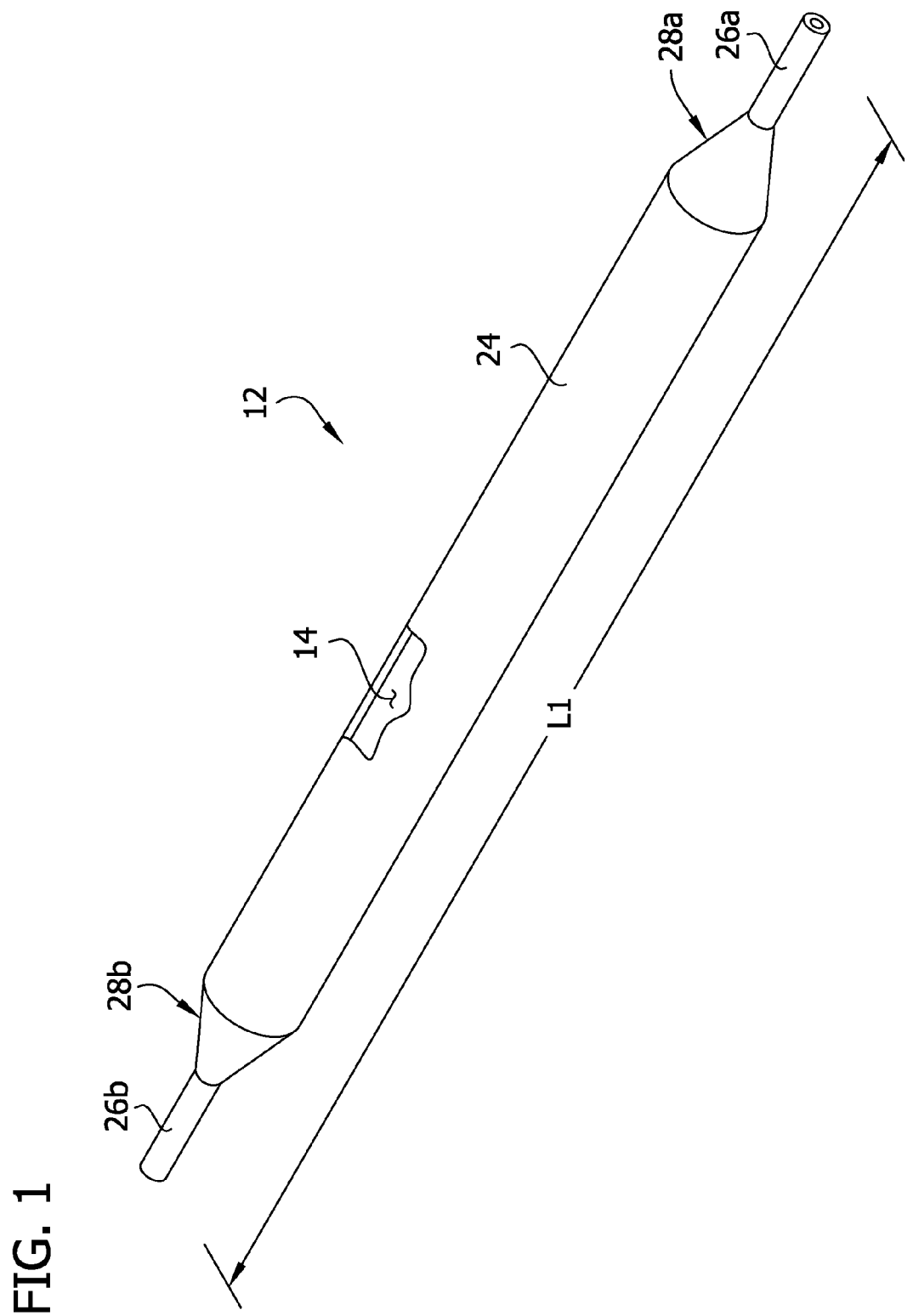
FIG. 1 is a perspective of one embodiment of a medical balloon for a balloon catheter.
Figure 2:
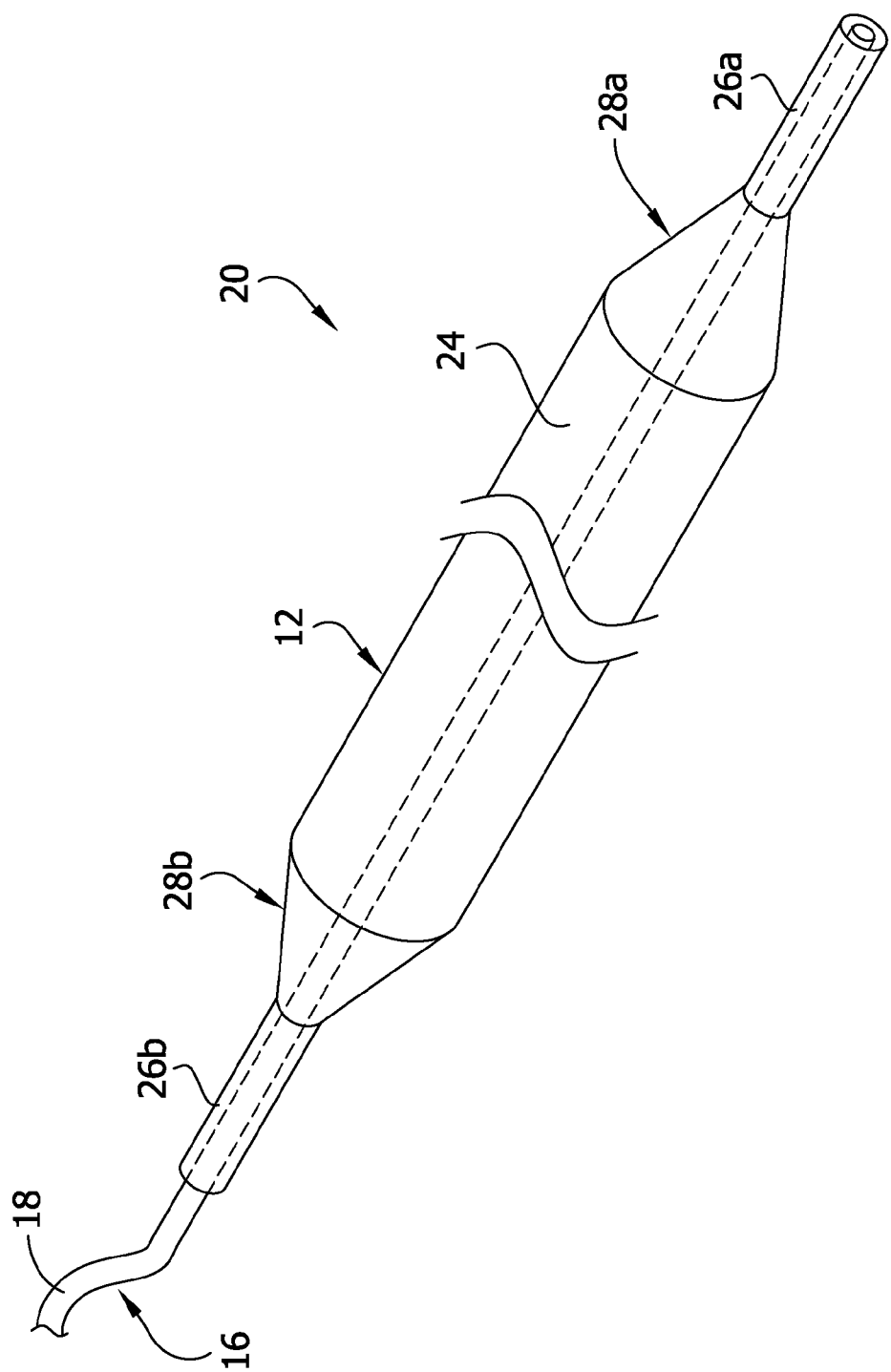
FIG. 2 is a fragmentary perspective of a balloon catheter including the balloon of FIG. 1.

Referring to FIG. 1, one embodiment of a medical balloon for a medical device is generally indicated at reference numeral 12 in FIG. 1. The balloon defines an interior chamber 14 for receiving fluid therein to expand an outer circumference (i.e., an outer perimeter) of the balloon. The balloon 12 is shown in its expanded or inflated configuration throughout the drawings, with the understanding that in its non-expanded configuration (e.g., deflated configuration or uninflated configuration), the balloon is capable of folding lengthwise such that the outer circumference of the balloon in its non-expanded configuration is substantially less than the outer circumference of the balloon in its expanded configuration. With respect to any or all of the below described embodiments of the present disclosure, the medical balloon 12 may be secured to a catheter, generally indicated at 16 in FIG. 2, such that a catheter body 18 of the catheter extends axially through the interior chamber 14 of the balloon, as is generally known in the art, to form a balloon catheter, generally indicated at 20. The balloon 12 and catheter body 18 have suitable shapes and dimensions for introduction into a desired body lumen for treatment therein. Typically, the balloon 12, in its non-expanded initial configuration (e.g., uninflated configuration), is introduced into the body lumen using an introducer sheath (not shown). The non-expanded balloon 12 is delivered to a treatment location within a body lumen (e.g., a blood vessel) by tracking through the introducer sheath and ultimately exiting a distal end of the sheath to reach the treatment location. Once the non-expanded balloon 12 has reached the treatment location, fluid (e.g., saline) is delivered into the balloon, thereby expanding the outer circumference of the balloon (e.g., balloon is inflated). After treatment, the balloon 12 is deflated to its non-expanded configuration and "pulled back" into the introducer sheath. The balloon catheter 20 can then be withdrawn from the introducer sheath and the patient's body. It may be necessary or desired to re-introduce the balloon catheter 20 into a body lumen, through the introducer sheath, to further treat the body lumen.

The illustrated balloon catheter 20 may be configured for introduction along and inflation (i.e., circumferential or perimeter expansion) within a blood vessel for treating vascular stenosis. As an example, the medical balloon 12 of the illustrated balloon catheter 20 may be configured for introduction along and expansion within one or more of peripheral arteries and veins, coronary arteries and veins, renal arteries and veins, cerebral arteries and veins, and carotid artery. In other examples, the medical balloon 12 may be configured for introduction along and expansion within other body lumens for treating stenosis of those lumens. The balloon 12 may be configured for treating other body lumens and/or for other treatments of those lumens.

Referring to FIG. 1, the medical balloon 12 has a length L1 and comprises a balloon body section 24; opposite distal and proximal waist sections 26a, 26b, respectively, at opposite longitudinal ends of the balloon; and opposite distal and proximal cone sections, generally indicated at 28a, 28b, respectively, at corresponding distal and proximal ends of the body section intermediate the body section and the corresponding distal and proximal waist sections. The length L1 of the balloon may measure from about 10 mm to about 250 mm. As explained in more detail below, the body section 24, waist sections 26a, 26b, and cone sections 28a, 28b may be integrally formed during a blow molding process to form the balloon 12 as a one-piece construction. It is understood that the balloon 12 may have other sections, structures, and/or components without departing from the scope of the present invention.

The balloon 12 may be formed from a polymer material, including, but not limited to, a thermoplastic polymer or a thermoplastic elastomer polymer. For example, suitable materials for the balloon include polyesters such as PET, PEN and PBT; polyurethane block copolymers such as ISOPLAST 301, PELLETHANE 2363-75D; polyamide block copolymers such as PEBAX 6333, PEBAX 7033 and PEBAX 7233; polyamides such as nylon 12, nylon 11, and nylon 10; polymer blend materials such as single or multiphase blends of liquid crystal polymers in another polymer; and polyester elastomer balloons such as ARNITEL EM 740 and HYTREL 8238. Other materials do not depart from the scope of the present invention as defined by the claims. In one example, the balloon 12 may be free from a lubricious coating (hydrophobic or hydrophilic), although in other examples the balloon may include such a lubricious coating.

Figure 3:
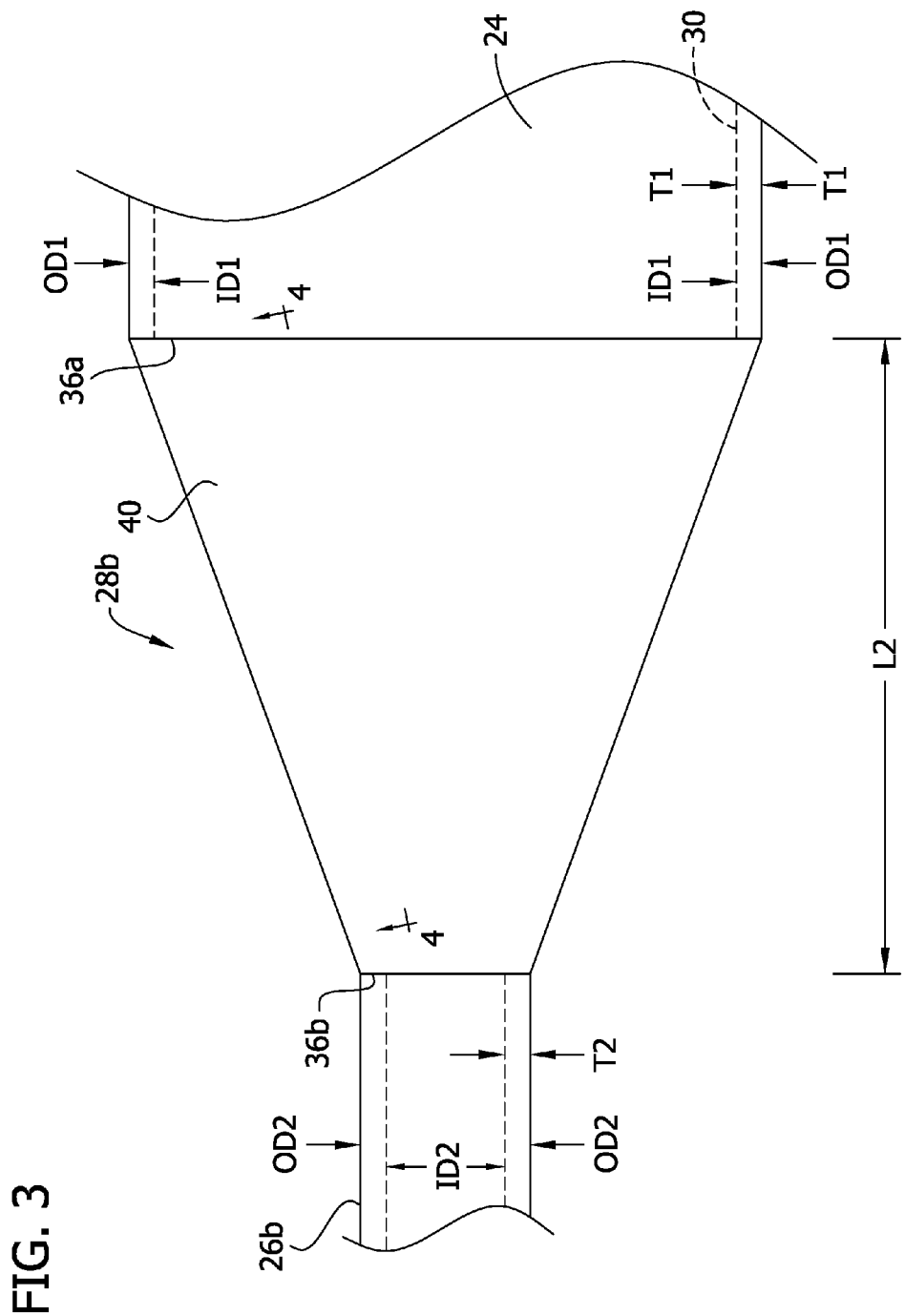
FIG. 3 is an enlarged, fragmentary side elevational view of the balloon of FIG. 1, showing a proximal cone section, a portion of a proximal waist section, and a portion of the body section thereof.

As shown in FIG. 1, the body section 24 interconnects and is disposed between the distal and proximal cone sections 28a, 28b. In the illustrated embodiment, the body section 24 is generally tubular defining a portion of the interior chamber 14 for receiving fluid to expand an outer circumference (i.e., an outer dimension) of the body section. Referring to FIG. 3, the body section 24 has an expanded inner diameter ID1 (i.e., an inner cross-sectional dimension) defined by an interior surface 30 of the balloon 12, an expanded outer diameter OD1, and a thickness T1 that may be generally uniform along its length. In one example, the expanded outer diameter OD1 may measure greater than or equal to about 3 mm, and in one example, from about 3 mm to about 30 mm, and the single-wall thickness T1 may measure from about 0.0127 mm to about 0.0762 mm. The body section 24 may have other shapes and dimensions without departing from the scope of the present invention.

The distal and proximal waist sections 26a, 26b are generally tubular and, in the illustrated embodiment, are configured to receive the catheter body 18 therein. Referring to FIG. 3, each waist section 26a, 26b has an outer diameter OD2 less than the outer diameter OD1 of the body section 24. Thicknesses T2 of the waist sections 26a, 26b may be greater than the thickness T1 of the body section 24. It is understood that the waist sections 26a, 26b may be omitted from the balloon 12 without departing from the scope of the present invention.

Figure 4:
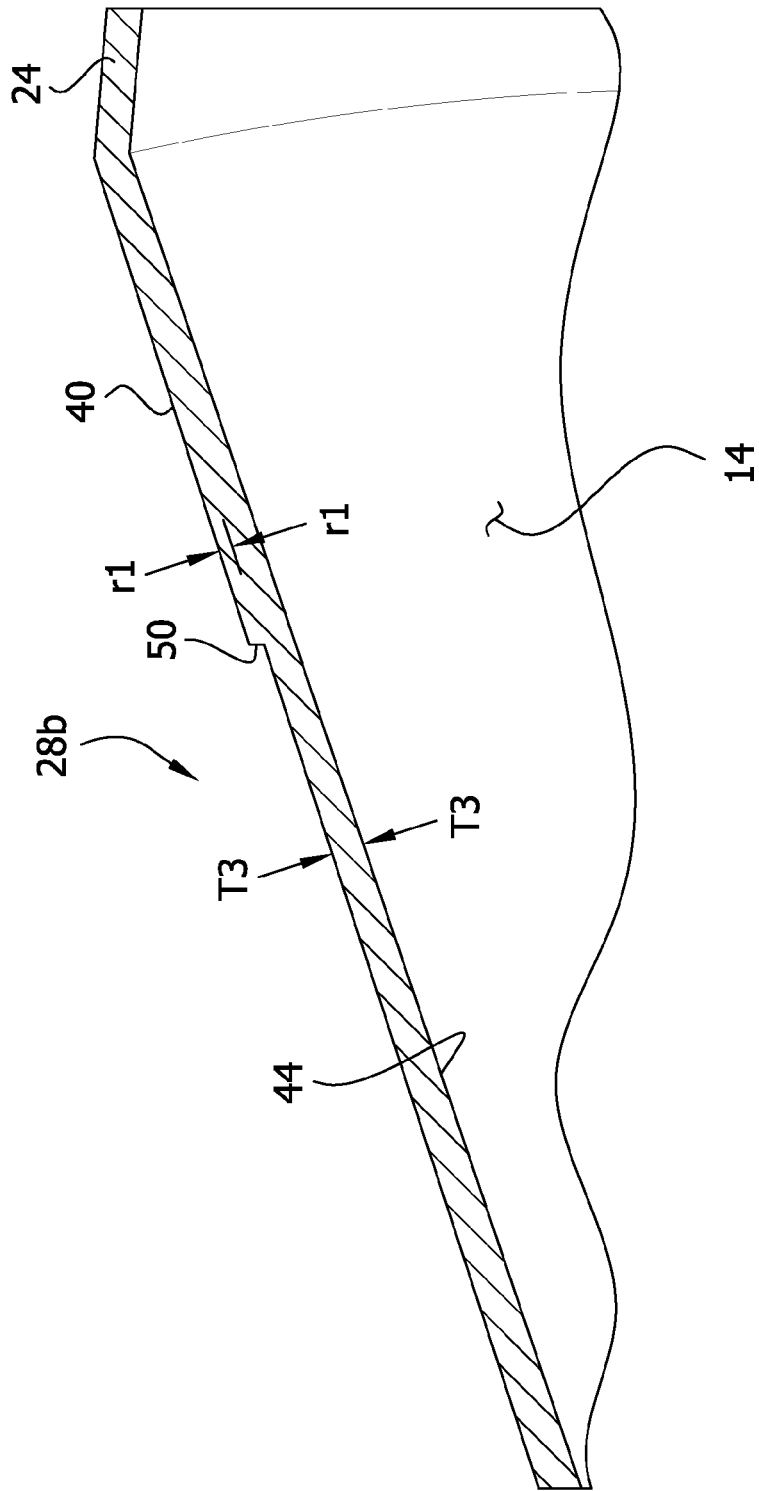
FIG. 4 is an enlarged, fragmentary section of the balloon taken along the line 4-4 in FIG. 3.

In general, the distal and proximal cone sections 28a, 28b are mirror images of one another. For purposes of this disclosure, the proximal cone section 28b is shown in detail in the drawings, with the understanding that the teachings relating to the proximal cone section apply equally to the distal cone section 28a, with exceptions noted herein. Referring to FIG. 3, the proximal cone section 28b has distal and proximal ends 36a, 36b, a length L2 extending between the proximal and distal ends, and an exterior surface 40 having a generally conical (e.g., frustoconical) shape and an outer diameter (i.e., an outer cross-sectional dimension) tapering proximal toward the proximal end of the proximal cone section. As shown in FIG. 4, an interior surface 44 of the proximal cone section 28b also has a generally conical shape defining an inner circumference or periphery (i.e., an inner dimension) and an inner diameter (i.e., an inner cross-sectional dimension) of the cone section that taper proximally toward its proximal end 36b. A reduced-thickness longitudinal portion (e.g., an apex end margin) of the proximal cone section 28b extending from the proximal end 36b of the cone section toward the distal end 36a thereof has a reduced wall thickness T3. The reduced wall thickness T3 extends around a 360-degree exterior perimeter of the reduced-thickness longitudinal portion of the proximal cone section 28b. As explained in more detail below, the reduced wall thickness T3 is formed by removing material from an exterior of the proximal cone section 28b. Because of the material removal process, the reduced-thickness longitudinal portion is coarser and more opaque than the remainder of the proximal cone section 28b. Moreover, a step transition 50 is formed on the exterior surface between the reduced-thickness longitudinal portion and the remainder of the proximal cone section 28b. The step transition 50 extends continuously around the 360 degree perimeter of the proximal cone section 28b such that the step transition has an annular shape. In a non-limiting example, the step transition 50 may have a radial dimension r1 from about 0.0254 mm to about 0.0508 mm.

In the illustrated embodiment, the structures of the distal cone section 28a have inverse relationships with the corresponding structures of the proximal cone section 28b. Although not shown in detail in the drawings, the distal cone section 28a has proximal and distal ends, a length extending between the proximal and distal ends, and an exterior surface having a generally conical shape and defining an outer circumference or periphery (i.e., an outer dimension) and an outer diameter (i.e., an outer cross-sectional dimension) of the cone section that taper distally toward its distal end. An interior surface of the distal cone section 28a also has a generally conical shape and defines an inner circumference or periphery (i.e., an inner dimension) and an inner diameter (i.e., an inner cross-sectional dimension) of the cone section that taper distally toward the distal end thereof. A reduced-thickness longitudinal portion (e.g., the apex end margin) of the distal cone section 28*a* extending from the distal end of the cone section toward the proximal end thereof has a reduced wall thickness, similar to the reduced wall thickness of the proximal cone section 28*b*. The reduced wall thickness extends around a 360-degree exterior perimeter of the reduced-thickness longitudinal portion of the distal cone section 28*a*. As explained in more detail below, the reduced wall thickness is formed by removing material from an exterior surface of the distal cone section 28*a*. Because of the material removal process, the reduced-thickness longitudinal portion is coarser and more opaque than the remainder of the distal cone section 28*a*. Moreover, a step transition is formed on the exterior between the reduced-thickness longitudinal portion and the remainder of the distal cone section 28*a*. The step transition extends continuously around the 360 degree perimeter of the distal cone section 28*a* such that the step transition has an annular shape. In a non-limiting example, the step transition may have a radial dimension from about 0.0254 mm to about 0.0508 mm.

Figure 5:
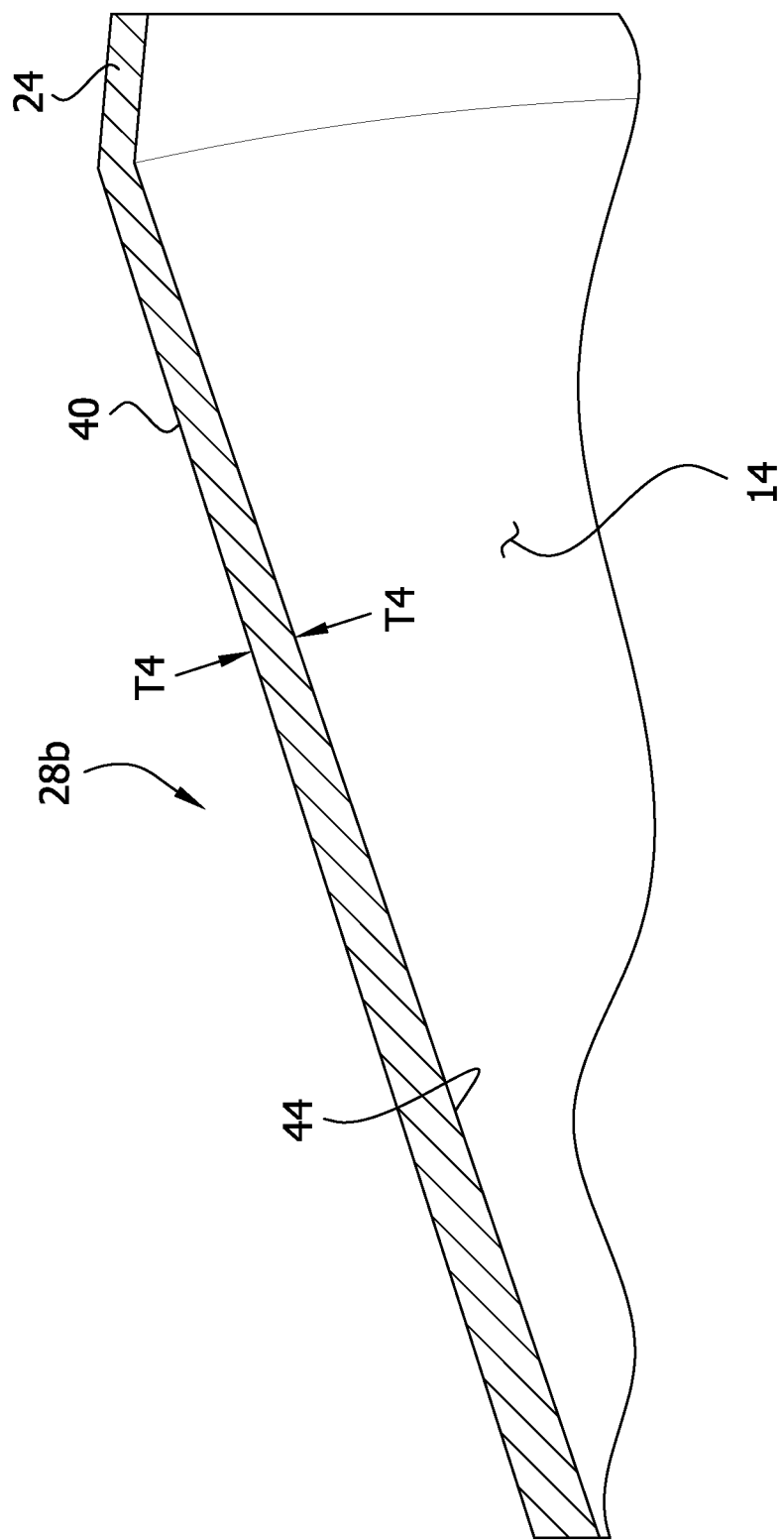
FIG. 5 is an enlarged, fragmentary section of the balloon, similar to FIG. 4, before removing material from the proximal cone section.

A cross section of an embodiment of a blow-molded balloon before removing material from the cone sections according to one embodiment of the present disclose is shown in FIG. 5. As shown in FIG. 5, a wall thickness T4 of the proximal cone section 28*b* between the interior and exterior surfaces 40, 44 generally increases toward the proximal end 36*b* thereof and the proximal waist section 26*b*, such that the proximal cone section has a maximum wall thickness generally adjacent to the proximal waist section. Likewise, a thickness (not indicated) of the distal cone section 28*a* between the interior and exterior surfaces generally increases toward the distal end thereof and the distal waist section, such that the distal cone section has a maximum wall thickness generally adjacent to the distal waist section. As set forth above, the wall thicknesses T4 of the proximal and distal cone sections 28*a*, 28*b* after blow molding may interfere with refolding of the balloon upon deflation (i.e., after treatment), which can make it difficult to pull the balloon back into the introducer sheath. Accordingly, the following disclosed method and material-removal machine for reducing the wall thickness T4 of at least one of the distal and proximal cone sections 28*a*, 28*b*, particularly the proximal cone section such as shown in FIG. 4, also reduces the amount of force required to pull the balloon 12 back into the introducer sheath.

Figure 6:
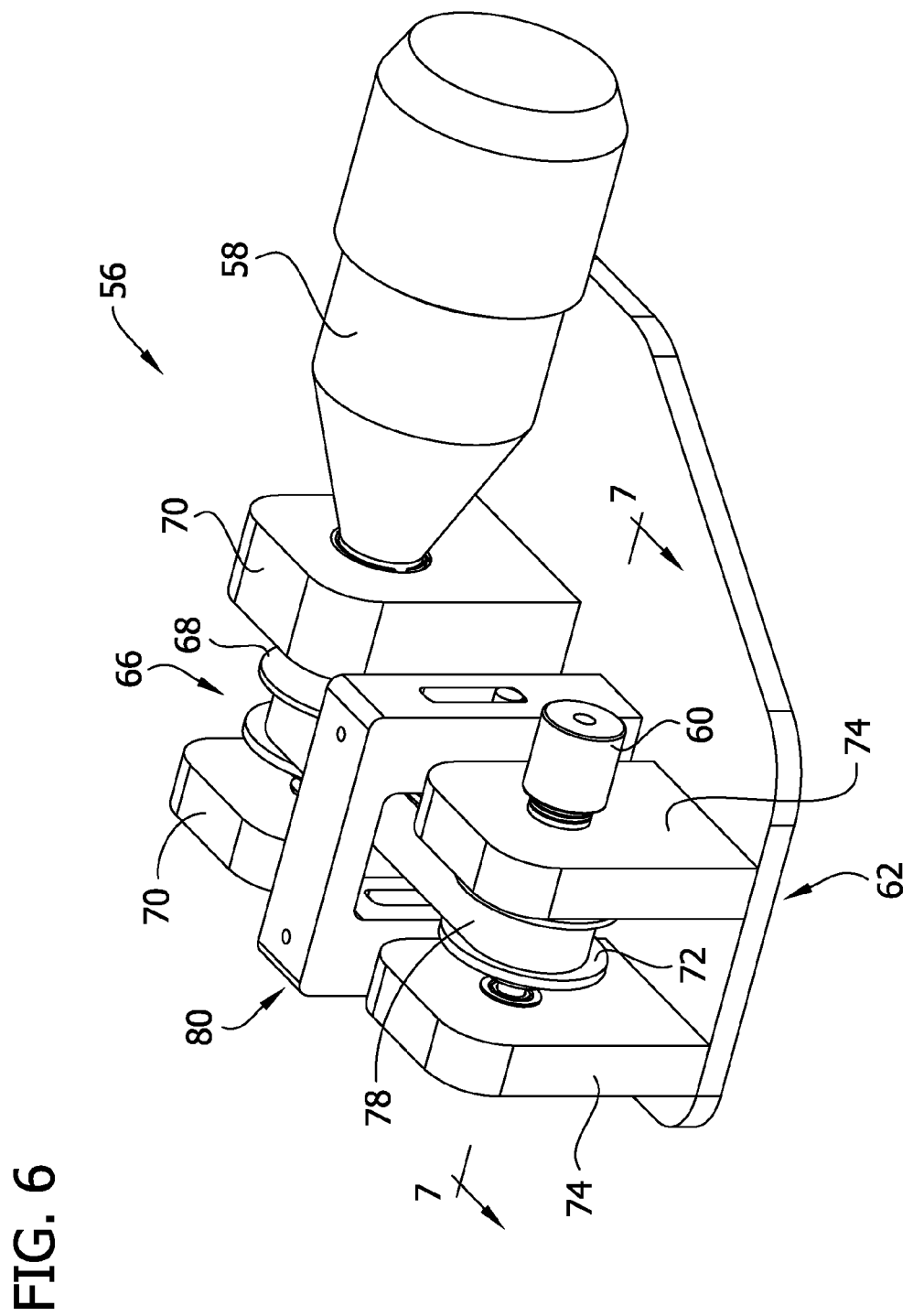
FIG. 6 is a perspective of a material-removing machine.
Figure 7:
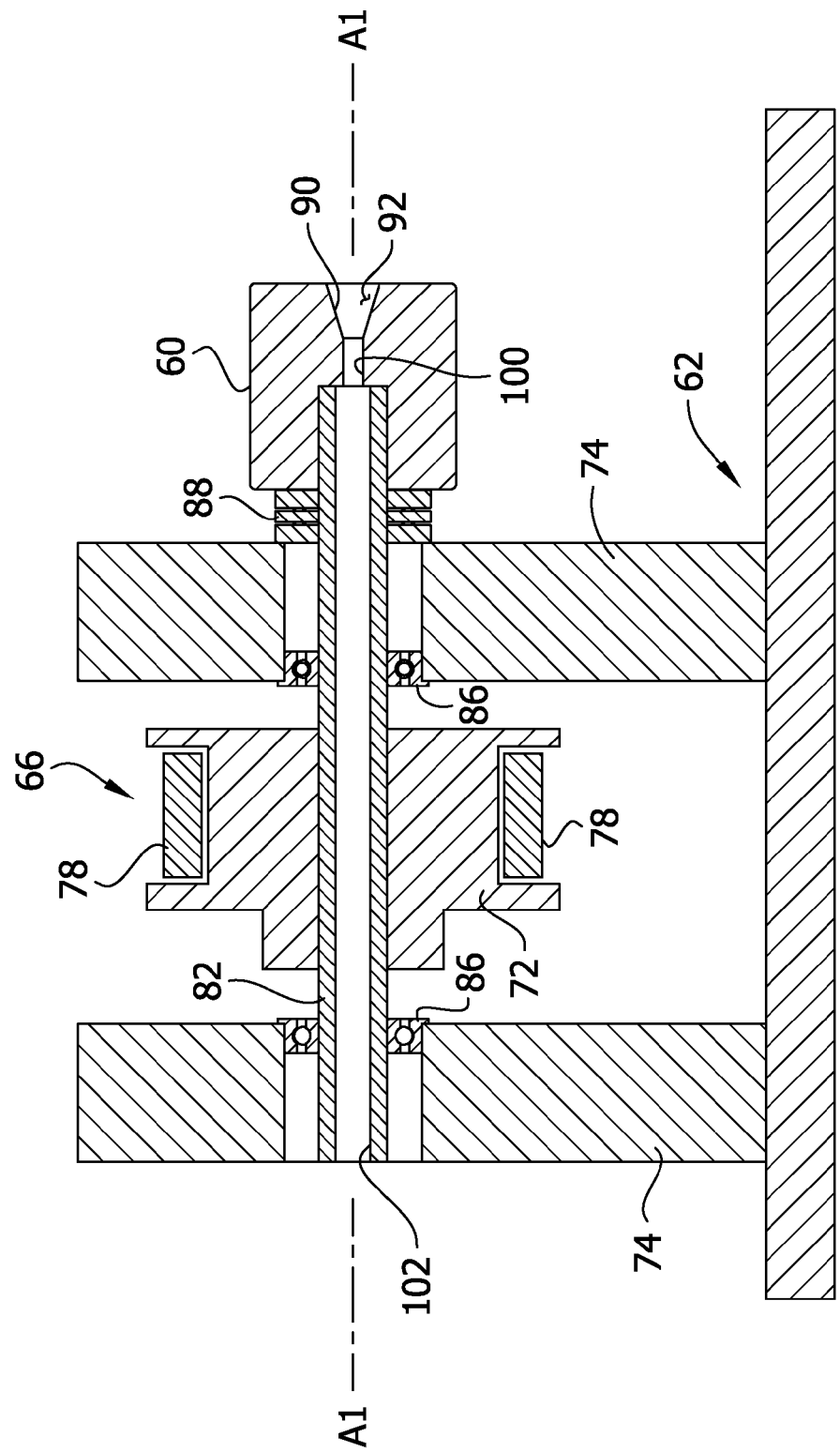
FIG. 7 is a cross section of the material-removing machine taken through the line 7-7 in FIG. 6.

Referring to FIG. 6, one embodiment of a material-removing machine is generally indicated at reference numeral 56. The material-removing machine 56 includes a prime mover 58 (e.g., an electric motor), a material-removing element 60 operatively connected to the prime mover such that operation of the prime mover imparts rotation to the material-removing element about a rotational axis A1, and a base, generally indicated at 62, to which the prime mover and the material-removing element are secured. In the illustrated embodiment, the prime mover 58 imparts rotation to the material-removing element 60 via a belt and pulley system, generally indicated at 66. The belt and pulley system 66 includes a driver pulley 68 mounted on a first pair of mounts 70 of the base 62, a driven pulley 72 mounted on a second pair of mounts 74, and a belt 78 connecting the driver and driven pulleys. The illustrated material-removing machine 56 also includes a belt tensioning mechanism, generally indicated at 80, to allow variable tensioning of the belt 78. The driver pulley 68 is fixed to and rotationally driven by the prime mover 58. Torque is transmitted from the driver pulley 68 to the driven pulley 72 via the belt 78. The driven pulley 72 is fixed to a drive shaft 82, which is in turn fixed to the material-removing element 60. Accordingly, the driven pulley 72 transmits torque to the drive shaft 82, which transmits torque to the material-removing element 60 for rotating the material-removing element about the rotational axis A1. As shown in FIG. 7, the drive shaft 82 is secured to the mounts 74 of the base 62 via radial bearings 86 and a thrust bearing 88 such that the drive shaft is rotatable relative to the base about the rotational axis A1. In other embodiments, the material-removing machine 56 may include a drive system other than the belt and pulley system 66, such as a direct drive system.

Figure 9:
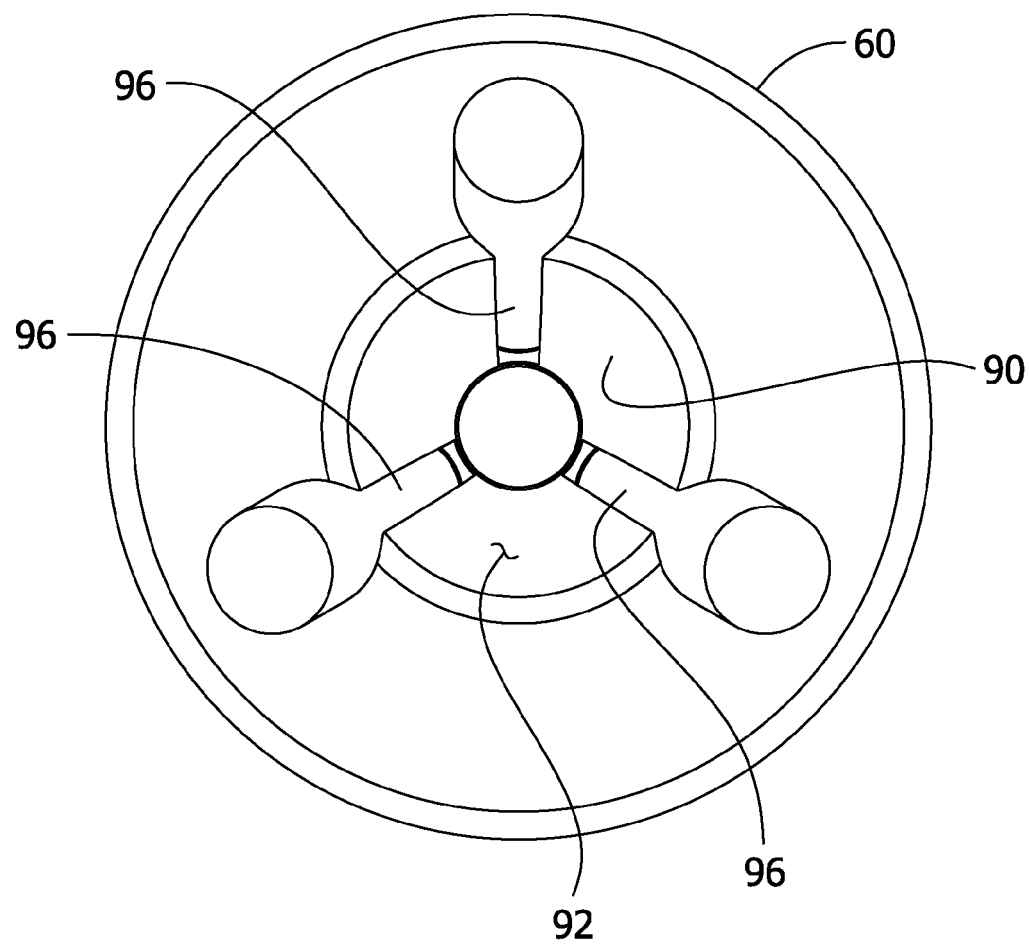
FIG. 9 is a front elevation of an embodiment of a material-removing element of the material-removing machine.

As shown in FIG. 7, the material-removing element 60 includes an interior surface 90 defining a generally conical-shaped cavity 92 extending along the rotational axis A1 and adapted to receive at least a longitudinal portion of a cone section 28*a*, 28*b* of the expanded medical balloon 12. At least a portion of the interior surface 90 is adapted to remove material from the longitudinal portion of the cone section 28*a*, 28*b* to reduce the wall thickness of the longitudinal portion. In one embodiment, at least a portion of the interior surface 90 of the material-removing element 60 may be defined by one or more abrasive elements for abrading the cone section 28*a*, 28*b* as the material-removing element rotates about the rotational axis A1. For example, as shown in FIG. 9, a plurality of abrading elements 96 (e.g., burrs) may define a portion of the interior surface 90. The material-removing element 60 also defines a through opening 100 in communication with the conical-shaped cavity 92. The through opening 100 is sized and shaped for receiving the waist section 26*a*, 26*b* of the expanded medical balloon 12 when the corresponding cone section 28*a*, 28*b* of the balloon is received in the conical-shaped cavity 92. The through opening 100 is also in communication with a passage 102 extending axially within the drive shaft 82. The passage 102 is configured to receive a shaft (e.g., the catheter body 18) that is secured to the proximal end of the balloon 12. The shaft 18 allows the balloon 12 to be expanded (e.g., inflated) during removal of material from one or more of the cones 28*a*, 28*b*. In the illustrated embodiment, the material-removing element 60 is removably secured to the drive shaft 82 via a set screw (not shown) or in other ways.

Figure 10:
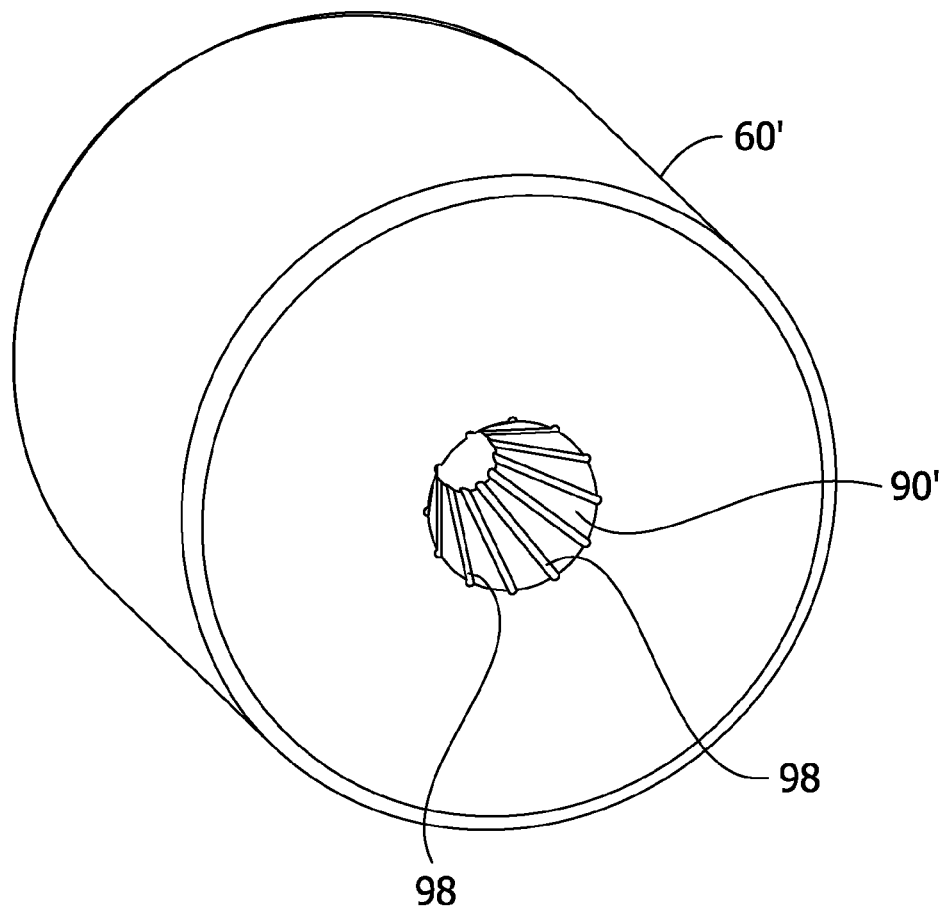
FIG. 10 is a perspective of another embodiment of a material-removing element.
Figure 11:
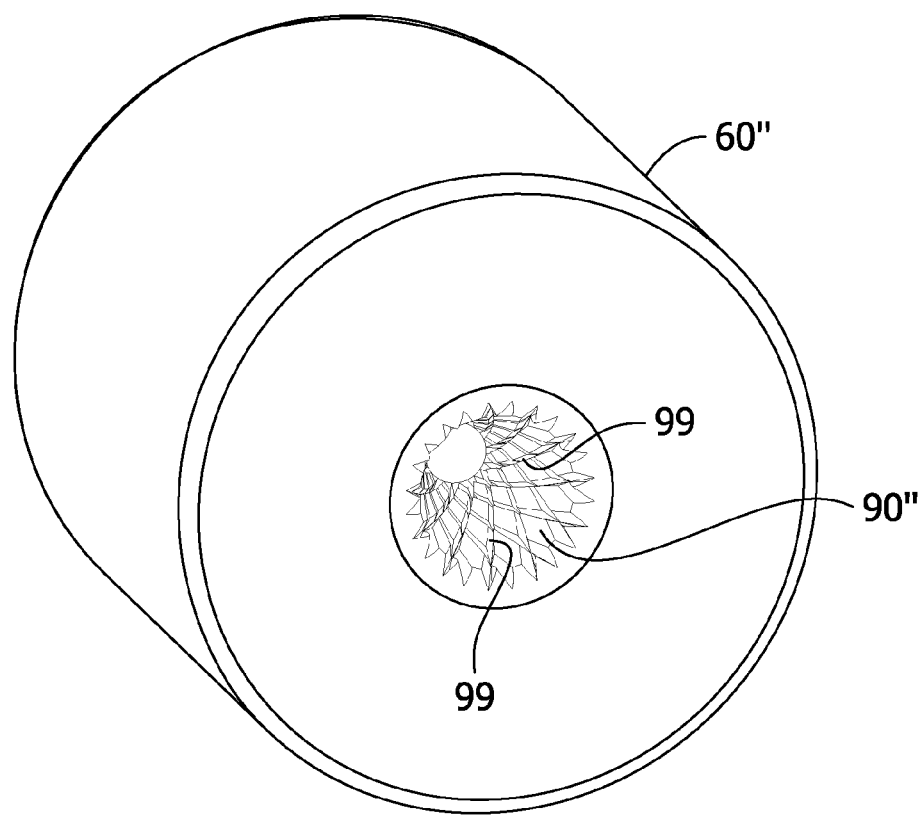
FIG. 11 is a perspective of yet another embodiment of a material-removing element.

In another embodiment, at least a portion of the interior surface 90 of the material-removing element 60 may be defined by one or more cutting elements for cutting the cone section 28*a*, 28*b* as the material-removing element rotates about the rotational axis A1. For example, in the embodiment shown in FIG. 10, an interior surface 90' of a material-removing element 60' includes straight grooves 98 defining ribs for removing material. In another example shown in FIG. 11, an interior surface 90" of a material-removing element 60" includes crossing helical grooves 99 defining a knurled surface for removing material. The material-removing element may include other elements for removing material from the cone section 28*a*, 28*b*.

In an exemplary method, material is removed from one or both of the cone sections 28*a*, 28*b* of an expanded medical balloon 12 using the illustrated material-removing machine 56, for example. The medical balloon 12 is expanded (e.g., inflated) into its expanded configuration by delivering a fluid (e.g., saline) into the interior chamber 14 of the medical balloon. The medical balloon 12 may be expanded before, during or after insertion of the respective cone section 28*a*, 28*b* into the conical-shaped cavity 92 of the material-removing element 60. In one example when removing material from the proximal cone section 28*b*, the shaft (e.g., catheter body 18) attached to the uninflated medical balloon 12 is first inserted through the conical-shaped cavity 92 and through the axial passage 102 of the drive shaft 82 such that a proximal end margin of the shaft extends through an open free end of the drive shaft. A holder (not shown) may be configured to hold or pull the free end of the waist section 26b such that the proximal cone section 28b is received and held within the conical-shaped cavity 92 and the proximal waist section 26b is received in the through opening 100. In another example when removing material from the distal cone section 28a, the distal cone section is received within the conical-shaped cavity 92 and the distal waist section 26a is inserted into the through opening 100. The medical balloon 12 may be expanded before, during or after insertion of the respective cone section 28a, 28b into the conical-shaped cavity 92 of the material-removing element 60. In one example, the medical balloon 12 is expanded after the cone section 28a, 28b is received in the conical-shape cavity 92. Moreover, in the illustrated embodiment, only the longitudinal portion of the cone section 28b is received in the material-removing element 60.

Figure 8:
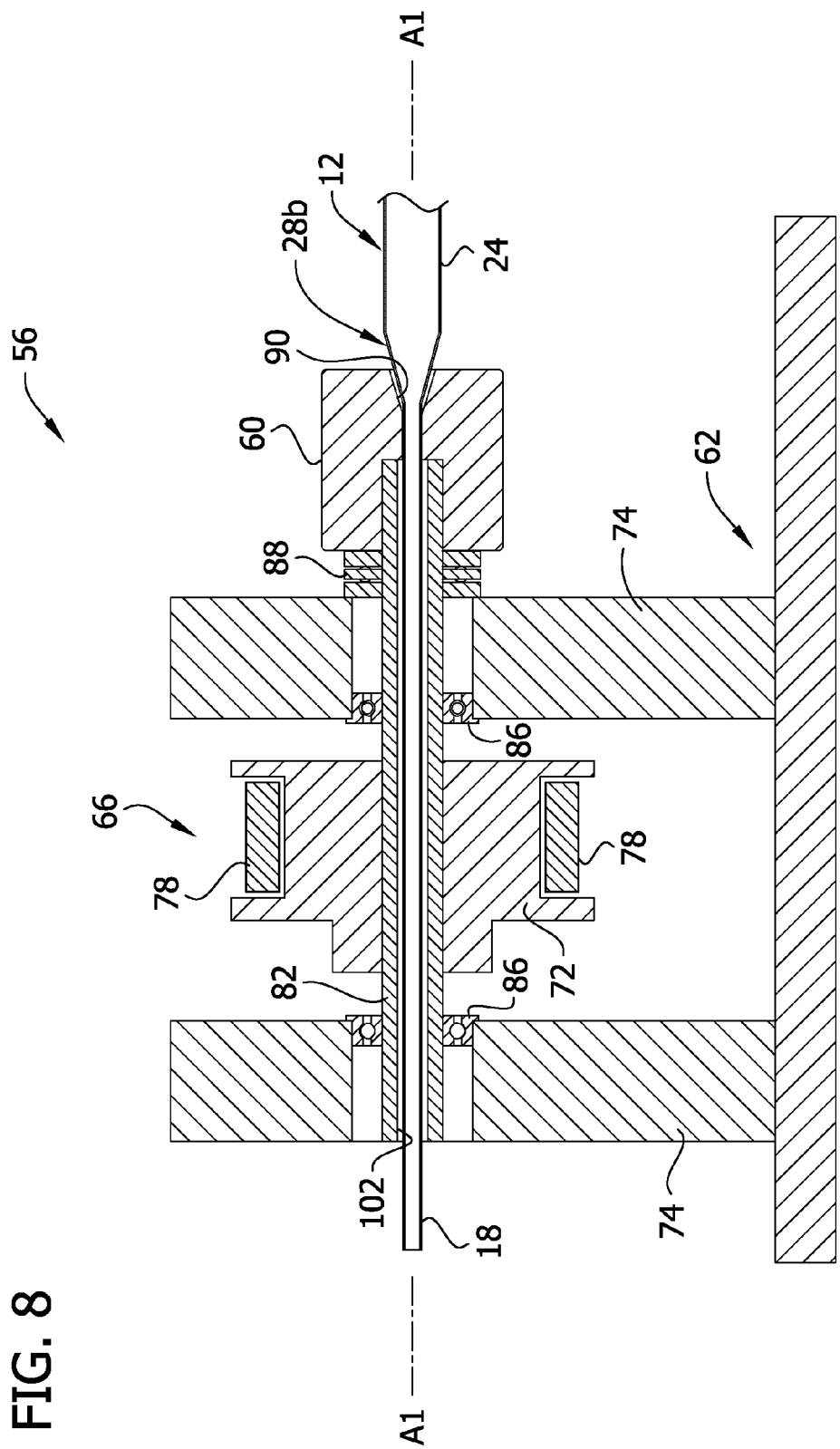
FIG. 8 is similar to FIG. 7, additionally including a cross section of an expanded medical balloon received in the material-removing machine.

Referring to FIG. 8, with the medical balloon 12 in its expanded configuration and the cone section 28b received in the material-removing element 60, the prime mover 58 is operated to rotate the material-removing element about the rotational axis A1. In a non-limiting example, the material removing element 60 may have a rotational speed from about 5,000 rpm to about 10,000 rpm. As the material-removing element 60 rotates about the cone section 28b, the material-removing element removes material continuously from the 360-degree exterior perimeter of the longitudinal portion of the cone section to reduce the wall thickness of the cone section. As a non-limiting example, the material-removing element 60 may be configured to remove from about 0.0254 mm to about 0.0508 mm of wall thickness from the 360-degree exterior perimeter of the longitudinal portion of the cone section 28b. The resulting cone section 28b may have the appearance and structure of the cone section 28b as described above with respect to FIG. 4. After removing material from the cone section 28b, material may be removed from the other cone section 28a in the same manner.

Having described the invention in detail, it will be apparent that modifications and variations are possible without departing from the scope of the invention defined in the appended claims.

When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above constructions, products, and methods without departing from the scope of the invention, it is intended that all matter contained in the above description and shown in the accompanying drawings shall be interpreted as illustrative and not in a limiting sense.

What is claimed is:

1. A material-removing machine for removing material from a cone section of a medical balloon comprising:
   a prime mover; and
   a material-removing element operatively connected to the prime mover such that operation of the prime mover imparts rotation to the material-removing element about a rotational axis, the material-removing element including an interior surface defining a generally conical-shaped cavity extending along the rotational axis and adapted to receive at least a longitudinal portion of a cone section of an expanded medical balloon, wherein at least a portion of the interior surface is adapted to remove material from the longitudinal portion of the cone section to reduce a wall thickness of the cone section.

2. The material-removing machine set forth in claim 1, wherein the conical-shaped cavity is adapted to receive less than an entirety of the longitudinal portion of the cone section of the expanded medical balloon.

3. The material-removing machine set forth in claim 2, wherein the conical-shaped cavity is adapted to receive an apex end margin of the cone section of the expanded medical balloon.

4. The material-removing machine set forth in claim 1, wherein the interior surface has a plurality of abrasive elements.

5. The material-removing machine set forth in claim 1, wherein the material-removing element further includes a through opening in communication with the conical-shaped cavity and adapted to receive at least a portion of a waist section extending outward from the cone section of the expanded medical balloon when at least the longitudinal portion of the cone section is received in the conical-shaped cavity.

6. The material-removing machine set forth in claim 1, further comprising a drive shaft operatively connected to the prime mover and the material-removing element for imparting rotation to the material-removing element, wherein the drive shaft defines a passage in communication with the conical-shaped cavity and configured to at least partially receive a shaft extending outward from the cone section.

7. A method of removing material from a cone section of a medical balloon, the method comprising:
   providing a medical balloon including a cone section defined by a balloon wall of the medical balloon having a thickness, wherein the medical balloon has a non-expanded configuration and an expanded configuration; and
   removing material continuously around a 360-degree exterior perimeter of at least a longitudinal portion of the cone section of the medical balloon to reduce the thickness of the balloon wall defining the cone section;
   wherein said removing material includes rotating a material-removing element 360 degrees around said at least a longitudinal portion of the cone section of the medical balloon.

8. The method of removing material from a cone section of a medical balloon as set forth in claim 7, wherein the medical balloon is in its expanded configuration during said removing material.

9. The method of removing material from a cone section of a medical balloon as set forth in claim 8, further comprising:
   expanding the medical balloon to its expanded configuration before said removing material.

10. The method of removing material from a cone section of a medical balloon as set forth in claim 7, wherein the cone section is at a proximal end of the medical balloon.

11. The method of removing material from a cone section of a medical balloon as set forth in claim 7, wherein said removing material includes disposing the cone section in a conical-shaped cavity of the material-removing element, wherein the conical-shaped cavity is defined by an interior surface of the material-removing element, at least a portion of the interior surface having a material-removing element.

12. The method of removing material from a cone section of a medical balloon as set forth in claim 11, wherein said removing material further includes rotating the material-removing element about a rotational axis.

13. The method of removing material from a cone section of a medical balloon as set forth in claim 11, wherein the medical balloon is in its expanded configuration during said removing material.

14. The method of removing material from a cone section of a medical balloon as set forth in claim 13, further comprising:
    expanding the medical balloon to its expanded configuration before said removing material.

15. The method of removing material from a cone section of a medical balloon as set forth in claim 11, further comprising:
    inserting, before said removing material, a waist section of the medical balloon into a passage in communication with the conical-shaped cavity of the material-removing element.

16. The method of removing material from a cone section of a medical balloon as set forth in claim 7, further comprising:
    removing material continuously around a 360-degree exterior perimeter of at least a longitudinal portion of another cone section of the medical balloon to reduce the thickness of the balloon wall defining the other cone section.

17. A method of removing material from a cone section of a medical balloon, the method comprising:
    providing a medical balloon including a cone section defined by a balloon wall of the medical balloon having a thickness, wherein the medical balloon has a non-expanded configuration and an expanded configuration;
    expanding the medical balloon to its expanded configuration;
    disposing at least a longitudinal portion of the cone section of the expanded medical balloon in a conical-shaped cavity defined by an interior surface of a material-removing element, wherein at least a portion of the interior surface is configured for removing material from the longitudinal portion of the cone section; and
    rotating the material-removing element about a rotational axis to remove material from an exterior perimeter of the cone section to reduce the thickness of the balloon wall defining the cone section.

18. The method of removing material from a cone section of a medical balloon as set forth in claim 17, further comprising:
    removing, simultaneously with said rotating, material around a 360-degree exterior perimeter of the longitudinal portion of the cone section of the medical balloon to reduce the thickness of the balloon wall defining the cone section.

19. The method of removing material from a cone section of a medical balloon as set forth in claim 17, further comprising:
    disposing at least a longitudinal portion of another cone section of the expanded medical balloon in the conical-shaped cavity;
    rotating the material-removing element about the rotational axis to remove material from an exterior perimeter of the other cone section to reduce the thickness of the balloon wall defining the other cone section.

20. The method of removing material from a cone section of a medical balloon as set forth in claim 17, further comprising:
    inserting, before said rotating, a shaft extending outward from the cone section of the medical balloon into a passage in communication with the conical-shaped cavity of the material-removing element.

* * * * *